US011229749B2

(12) United States Patent
Biederman et al.

(10) Patent No.: US 11,229,749 B2
(45) Date of Patent: Jan. 25, 2022

(54) PLATE CAPACITOR FOR DOSAGE SENSING (71) Applicant: Verily Life Sciences LLC, South San Francisco, CA (US)

(72) Inventors: William Biederman, San Francisco, CA (US); Louis Jung, Foster City, CA (US); Sean Frick, San Francisco, CA (US); Benjamin Collins, San Francisco, CA (US); Eric Bennett, Foster City, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 316 days.

(21) Appl. No.: 16/559,337

(22) Filed: Sep. 3, 2019

(65) Prior Publication Data
US 2020/0078527 A1 Mar. 12, 2020

Related U.S. Application Data
(60) Provisional application No. 62/727,810, filed on Sep. 6, 2018.

(51) Int. Cl.
*A61M 5/31* (2006.01)
*A61M 5/315* (2006.01)

(52) U.S. Cl.
CPC .... *A61M 5/31568* (2013.01); *A61M 5/31586* (2013.01); *A61M 2205/3317* (2013.01);
(Continued)

(58) Field of Classification Search
CPC ............ A61M 5/31568; A61M 5/3155; A61M 5/31586; G16H 20/17
See application file for complete search history.

(56) References Cited

U.S. PATENT DOCUMENTS 6,492,911 B1    12/2002  Netzer
7,008,399 B2     3/2006  Larsen et al.
(Continued)

FOREIGN PATENT DOCUMENTS

EP        2060284 A1    5/2009
WO   2016/071912 A1    5/2016
(Continued)

OTHER PUBLICATIONS

International Search Report & Written Opinion dated Nov. 11, 2019 for corresponding International Application No. PCT/US2019/049755, 11 pages.

*Primary Examiner* — Nathan R Price
*Assistant Examiner* — Courtney B Fredrickson
(74) *Attorney, Agent, or Firm* — Christensen O'Connor Johnson Kindness PLLC (57) ABSTRACT

A dosage measurement system is adapted to receive a motion from a dosage injection mechanism disposed within a drug injection pen. The dosage measurement system includes a substrate, a sensing capacitor disposed on the substrate, and a lifting tab. The sensing capacitor includes a dielectric layer disposed between a base plate and an adjustable plate. The lifting tab is attached to the adjustable plate and positioned to engage an undulation pattern disposed on a component attached to the dosage injection mechanism. The lifting tab is adapted to physically change a separation distance between the adjustable plate and the base plate in a reciprocal manner in response to the motion of the dosage injection mechanism and engagement with the undulation pattern. A capacitance of the sensing capacitor changes in response to the engagement of the lifting tab with the undulation pattern and the motion of the dosage injection mechanism.

20 Claims, 7 Drawing Sheets (52) U.S. Cl.
CPC ............... *A61M 2205/3386* (2013.01); *A61M 2205/3561* (2013.01); *A61M 2205/50* (2013.01); *A61M 2205/8206* (2013.01)

(56) References Cited

U.S. PATENT DOCUMENTS

| | | |
|---|---|---|
| 7,757,567 B2 | 7/2010 | Joyce et al. |
| 7,830,138 B2 | 11/2010 | Wolf et al. |
| 7,988,660 B2 | 8/2011 | Byland et al. |
| 8,057,434 B2 | 11/2011 | Burroughs et al. |
| 8,556,867 B2 | 10/2013 | Krulevitch |
| 8,638,108 B2 | 1/2014 | Nielsen et al. |
| 8,994,382 B2 | 3/2015 | Nielsen et al. |
| 9,186,465 B2 | 11/2015 | Jørgensen et al. |
| 9,289,559 B2 | 3/2016 | Pedersen et al. |
| 9,526,842 B2 | 12/2016 | Oh et al. |
| 9,561,330 B2 | 2/2017 | Draper |
| 9,623,188 B2 | 4/2017 | Nielsen et al. |
| 9,675,761 B2 | 6/2017 | Hoeholt et al. |
| 9,775,957 B2 | 10/2017 | Despa et al. |
| 2011/0313349 A1 | 12/2011 | Krulevitch et al. |
| 2014/0243750 A1 | 8/2014 | Larsen et al. |
| 2015/0352288 A1 | 12/2015 | Andersen |
| 2016/0051760 A1 | 2/2016 | Krusell et al. |
| 2016/0051764 A1 | 2/2016 | Dreier et al. |
| 2016/0287804 A1 | 10/2016 | Madsen et al. |
| 2017/0028124 A1 | 2/2017 | Deak et al. |
| 2017/0056581 A1 | 3/2017 | Deak et al. |
| 2017/0151388 A1 | 6/2017 | Monrad et al. |
| 2017/0224927 A1 | 8/2017 | Windum et al. |
| 2017/0232203 A1 | 8/2017 | Krusell |
| 2017/0286638 A1 | 10/2017 | Searle et al. |
| 2017/0290988 A1 | 10/2017 | Monrad et al. |
| 2018/0064879 A1 | 3/2018 | Sall et al. |
| 2018/0126088 A1 | 5/2018 | Radmer et al. |
| 2019/0009032 A1* | 1/2019 | Hautaviita ........ A61M 5/31593 |
| 2019/0022328 A1 | 1/2019 | Schleicher et al. |
| 2019/0321559 A1* | 10/2019 | Sheridan ............. A61M 5/2422 |

FOREIGN PATENT DOCUMENTS

| | | |
|---|---|---|
| WO | 2017/013463 A1 | 1/2017 |
| WO | 2017/013464 A1 | 1/2017 |
| WO | 2017050781 A1 | 3/2017 |
| WO | 2017/114768 A1 | 7/2017 |
| WO | 2019121617 A1 | 6/2019 |
| WO | 2019129621 A1 | 7/2019 |

* cited by examiner

PLATE CAPACITOR FOR DOSAGE SENSING

CROSS-REFERENCE TO RELATED APPLICATIONS

This application claims the benefit of U.S. Application No. 62/727,810, filed on Sep. 6, 2018, the contents of which are incorporated herein by reference.

TECHNICAL FIELD

This disclosure relates generally to fluid dispensing apparatuses and in particular but not exclusively, relates to tracking dispensed quantities of a fluid from a drug injection apparatus.

BACKGROUND INFORMATION

Measuring the quantity and recording the timing of a drug's administration is an integral part of many disease treatments. For many treatments, to achieve the best therapeutic effect, specific quantities of a drug may need to be injected at specific times of day. For example, individuals suffering from diabetes may need to inject themselves regularly throughout the day in response to measurements of their blood glucose. The frequency and volume of insulin injections should be carefully tracked and controlled to keep the patient's blood glucose level within a healthy range.

Currently, there are a limited number of methods or devices capable of tracking drug administration without requiring the user to manually measure and record the volume, date, and time. A variety of glucose injection syringes/pens have been developed, but there is much room for significant advancement in the technology in order to reduce the size, lower the cost, enhance the functionality, and improve the accuracy. Thus, the current technology may not be an ideal long-term solution. For example, current insulin pens are often disposable, but do not include dosage tracking. A smaller portion of the market is composed of reusable pens which are more expensive, and still do not include accurate dosage-tracking capabilities.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus, system, and method of operation for a dosage measurement system using an adjustable plate capacitor are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In a drug injection pen (like the one depicted in FIG. 1), there may be many mechanical moving components (e.g., a system to dial a dosage, a leadscrew to expel the dosage from the medication cartridge, etc.). One or more sensing capacitors with an adjustable plate may be used to track the absolute (rotational) position of some of the rotating components within the drug injection pen. As will be explained in greater detail below, tracking the position of these moving parts within the drug injection pen may be used to track a dosage (e.g., volume) of fluid dispensed from the drug injection pen.

Figure 1:
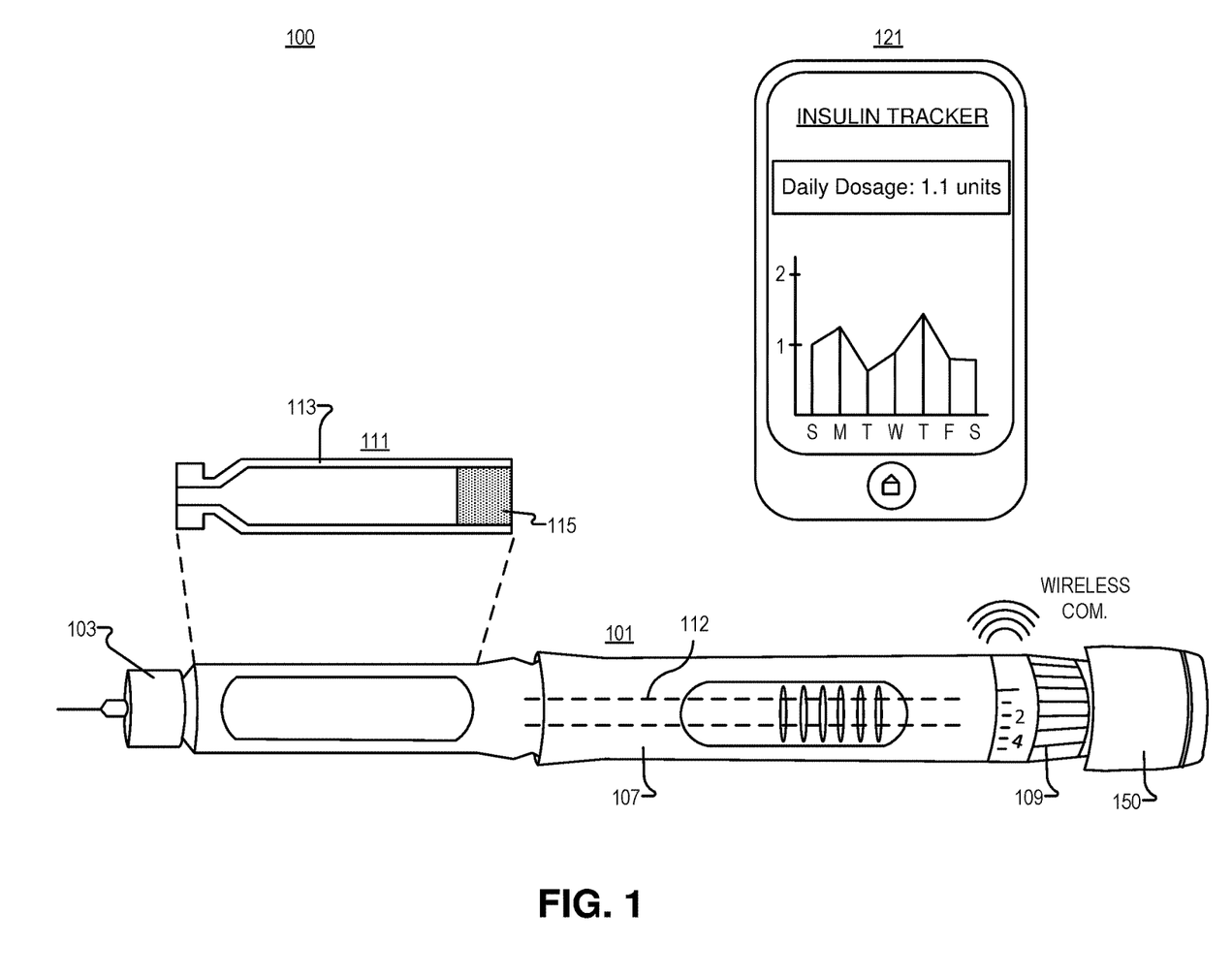
FIG. 1 illustrates an injection system, in accordance with an embodiment of the disclosure.

FIG. 1 illustrates an injection system 100, in accordance with an embodiment of the disclosure. The illustrated embodiment of system 100 includes drug injection pen 101, drug cartridge 111, and a processing device 121 (e.g., a smart phone).

Drug cartridge 111 includes cartridge body 113, and plunger head 115. In the depicted embodiment, plunger head 115 starts near the rear of drug cartridge 111 and is pushed forward in drug cartridge 111 (with a dosage injection mechanism—shown as dashed lines 112—disposed in injection pen 101). This forces medication/fluid out of the narrow end of drug cartridge 111 when a user chooses to dispense a fluid. In one embodiment, cartridge body 113 includes borosilicate glass.

Injection pen 101 is a hand-held device and includes needle 103, body/housing 107 (including dosage injection mechanism 112 to push in plunger head 115 and expel fluid from drug cartridge 111), and drug delivery control wheel 109 (e.g., twist wheel to "click" select the dosage), and pen button 150 (e.g., a push button for pushing with a thumb to dispense the selected quantity of the fluid from cartridge 111). It is appreciated that in some embodiments, pen button 150 may include a dosage measurement system (see e.g., FIGS. 2A and 2B) and the drug delivery control wheel 109. As shown, housing 107 is configured to accept cartridge 111: cartridge 111 may be disposed in an insert which screws/snaps onto the bulk of housing 107. However, as one of ordinary skill in the art will appreciate, drug injection pen 101 can take other configurations and have other components.

As stated, drug injection pen 101 includes a housing/body 107 shaped to accept a cartridge containing a fluid, and also includes a dosage injection mechanism positioned in the housing 107 to produce a motion (e.g., rotational motion) and force the fluid out of the cartridge when the drug injection pen 101 dispenses the fluid. A dosage measurement system is also disposed in the pen (e.g., in button 150 or elsewhere in pen body 107) to receive the motion from the dosage injection mechanism. As described herein, the dosage measurement system measures and tracks changes in capacitance of a sensing capacitor having an adjustable plate that moves in a reciprocal manner in response to the rotation of an undulation pattern disposed on a substrate that is coupled to rotate relative to a substrate upon which the sensing capacitor is mounted. The changes in the capacitance of the sensing capacitor are indicative of the motion received from the dosage injection mechanism, and if tracked over a time period, enable determination of the volume of a fluid dispensed over that time period.

A controller is also disposed in drug injection pen 101, and included with the dosage measurement system. The controller includes logic that when executed by the controller causes the controller to record a signal output from capacitance change detection circuitry coupled with the sensing capacitor. Changes in the signal are indicative of changes in the capacitance of the sensing capacitor, which changes as the fluid is dispensed. One of ordinary skill in the art will appreciate that the controller may be static (e.g., have logic in hardware), or dynamic (e.g., have programmable memory that can receive updates). In some embodiments, the controller may register the electrical signal output from the capacitance change detection circuitry as an injection event of the fluid, and the controller may calculate a quantity of the fluid dispensed based, at least in part, on a number of the injection events of the fluid registered by the controller. It is appreciated that this circuitry, which will be described in greater detail in connection with other figures, may be disposed anywhere in drug injection pen 101 (e.g., in body/housing 107 or pen button 150), and in some instances, logic may be distributed across multiple devices.

Processing device 121 (e.g., a smartphone, tablet, general purpose computer, distributed system, servers connect to the internet, or the like) may be coupled to receive dosage data from drug injection pen 101 to store/analyze this data. For instance, in the depicted embodiment, processing device 121 is a smartphone, and the smartphone has an application running recording how much insulin has been dispensed from drug injection pen 101. Moreover, the application is plotting how much insulin has been injected by the user over the past week. In this embodiment, a power source is electrically coupled to the controller in drug injection pen 101, and a transceiver is electrically coupled to the controller to send and receive data to/from processing device 121. Here, data includes information indicative of a quantity of the fluid dispensed over a period of time. The transceiver may include Bluetooth, RFID, or other wireless communications technologies.

Figure 2A:
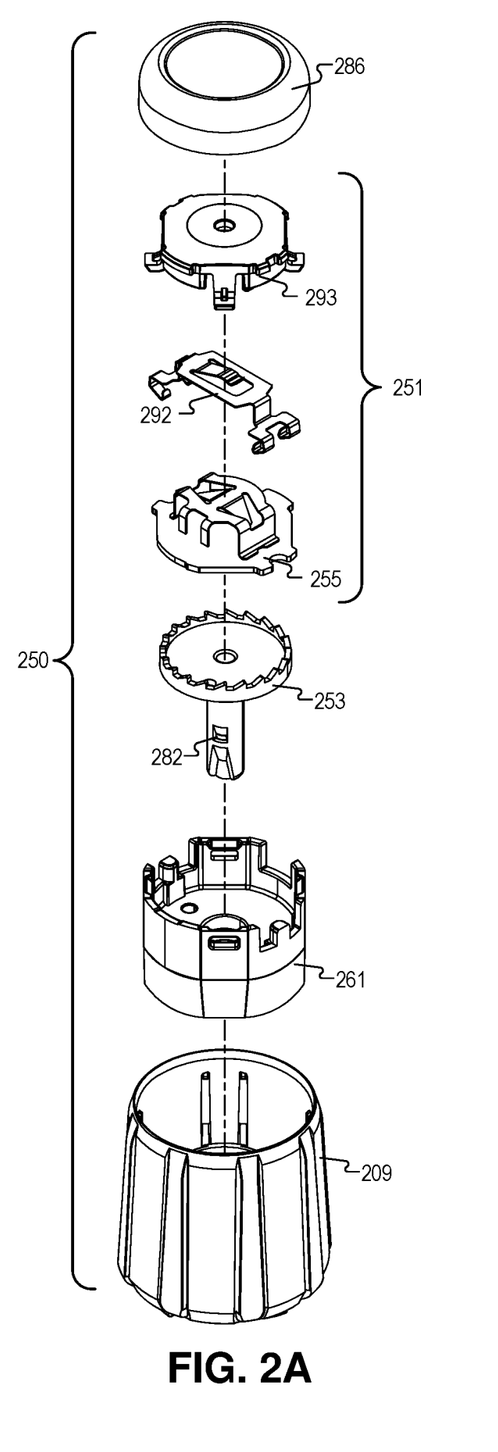
FIGS. 2A-2B are exploded view illustrations of the pen button depicted in FIG. 1 that includes a dosage measurement system, in accordance with an embodiment of the disclosure.
Figure 2B:
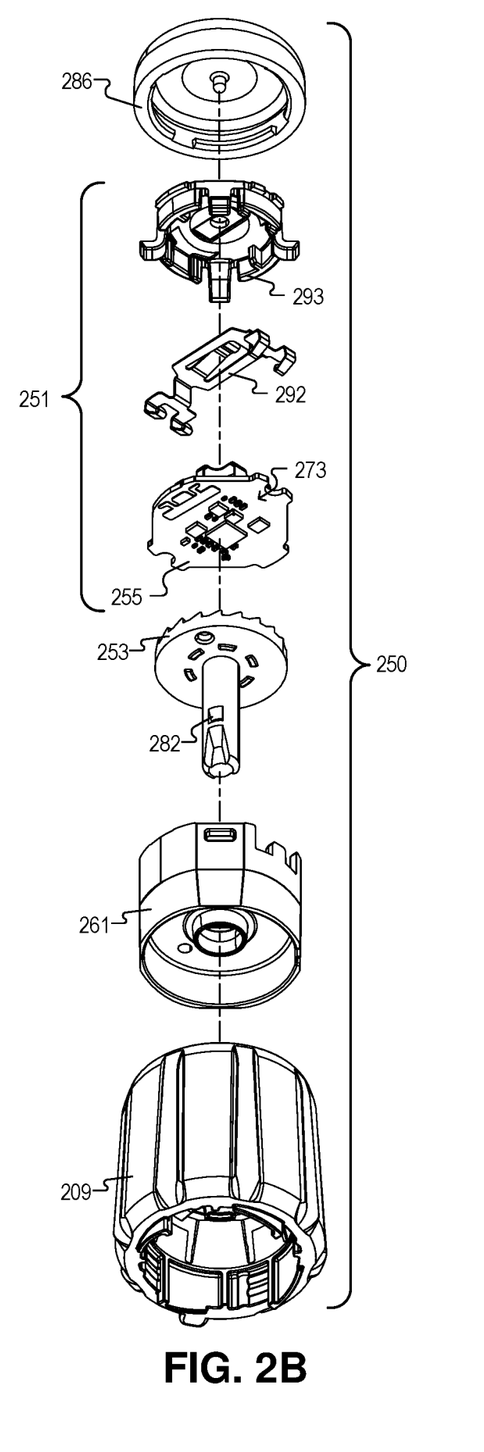

FIGS. 2A-2B illustrate an exploded view of a pen button 250 that attaches to an end of a drug injection pen, in accordance with an embodiment of the disclosure. Pen button 250 is one possible implementation of pen button 150 illustrated in FIG. 1. FIGS. 2A and 2B illustrate the same embodiment of pen button 250, but FIG. 2A illustrates an exploded view looking from the top down while FIG. 2B illustrates an exploded view looking from the bottom up. It is appreciated that pen button 250 may have different form factors than depicted. The illustrated embodiment of pen button 250 includes a drug delivery control wheel 209 (also known as a "dial grip"), a housing 261, a locking tab 282, a toothed component 253 (e.g., having a pedestal shape and an undulation pattern disposed thereon), a substrate 255 (e.g., circuit board), electronics 273, a retaining spring 292, a housing clip 293, and a spinner 286. The illustrated embodiment of electronics 273 includes a controller, one or more sensing capacitors, an optional reference capacitor, capacitance change detection circuitry, and a wireless communication interface (e.g., a transceiver). As shown, substrate 255, electronics 273, retaining spring 292, and housing clip 293 are disposed in dosage measurement system 251. In one embodiment, locking tab 282 and toothed component 253 may be considered part of and/or coupled with/to the dosage injection mechanism. In other embodiments, the undulation pattern may be disposed on a component that is part of dosage measurement system 251 and coupled to the dosage injection mechanism.

In some embodiments, spinner 286 may be made from polybutylene terephthalate (e.g., Celanex 2404MT). Spinner 286 may interact mechanically with (and bear on) housing 261, housing clip 293, and retaining spring 292. Housing clip 293 may be made from polycarbonate (e.g., Makrolon 2458). In the illustrated embodiment, housing clip 293 snap fits to housing 261, and spinner 286 bears on housing clip 293. Toothed component 253 (e.g., also referred to as a spindle) may also be made from polycarbonate, and snaps into a clutch in the pen. Toothed component 253 may also bear on housing 261. Housing 261 may be made from polyoxymethylene (e.g., Hostaform MT8F01). Housing 261 may bear on a clutch within the drug injection pen, spinner 286, and a linear slide track on the drug delivery control wheel 209. Drug delivery control wheel 209 may also be made from polycarbonate, and interacts with the linear slide track on housing 261.

In operation, the components may move together according to the following steps (discussed from a user-fixed reference frame). A user may dial a dose using drug delivery control wheel 209. The user presses down on spinner 286 with their thumb. Spinner 286 presses housing 261 down. Housing 261 presses the clutch inside the pen body down, and the clutch disengages. Drug delivery control wheel 209 and housing 261 will spin with the substrate 255 as the drugs are dispensed and toothed component 253/spinner 286 stay rotationally stationary. Thus, drug delivery control wheel 209, housing 261, and substrate 255 are mechanically coupled to rotate when fluid is dispensed. Tabs on substrate 255 interact with features on the inside of housing 261 to spin substrate 255. It is noteworthy that while dialing a dose, there may be no relative motion between toothed component 253 and substrate 255, but while dispensing, substrate 255 rotates relative to toothed component 253, which is fixed to the user-reference frame. In other embodiments, the relative motion may occur while dialing in a dose prior to actually dispensing the fluid. In such embodiments, the delivery control wheel or dial grip may be considered part of the dosage injection mechanism.

In some embodiments, toothed component 253 is connected to the clutch (contained in the pen body and included in the dosage injection mechanism)—these parts may not move relative to one another. The clutch is connected to the drive sleeve (also included in the dosage injection mechanism)—which moves axially relative to the clutch with about 1 mm range of motion. The leadscrew is threaded into the drive sleeve. If the user has dialed a dose and applies force to button 250, the clutch releases from the numbered sleeve and the leadscrew is pushed through a threaded "nut" in the pen body causing the leadscrew to advance. When the leadscrew advances, it presses on the rubber stopper in the medication vial to dispense fluid. It should be appreciated that the instant application is not intended to be limited to any particular dosage injection mechanism, but rather is intended to be broadly applicable to a variety of dosage injection mechanisms that generate a variety of motion types including rotational or linear motions.

In the depicted embodiment, one or more sensing capacitors are disposed on substrate 255. The sensing capacitors have an adjustable plate coupled to a lifting tab that engages the undulation pattern disposed around toothed component 253. As substrate 255 rotates relative to the undulation pattern on toothed component 253, the lifting tab physically moves the adjustable plate relative to a stationary base plate in a reciprocal manner in response to engaging the undulation pattern. As substrate 255 rotates relative to toothed component 253 in response to the motion (e.g., rotational or linear motion) from the dosage injection mechanism, the capacitance of the sensing capacitor changes. Tracking these changes over time enables the dosage tracking functionality described above.

Figure 3A:
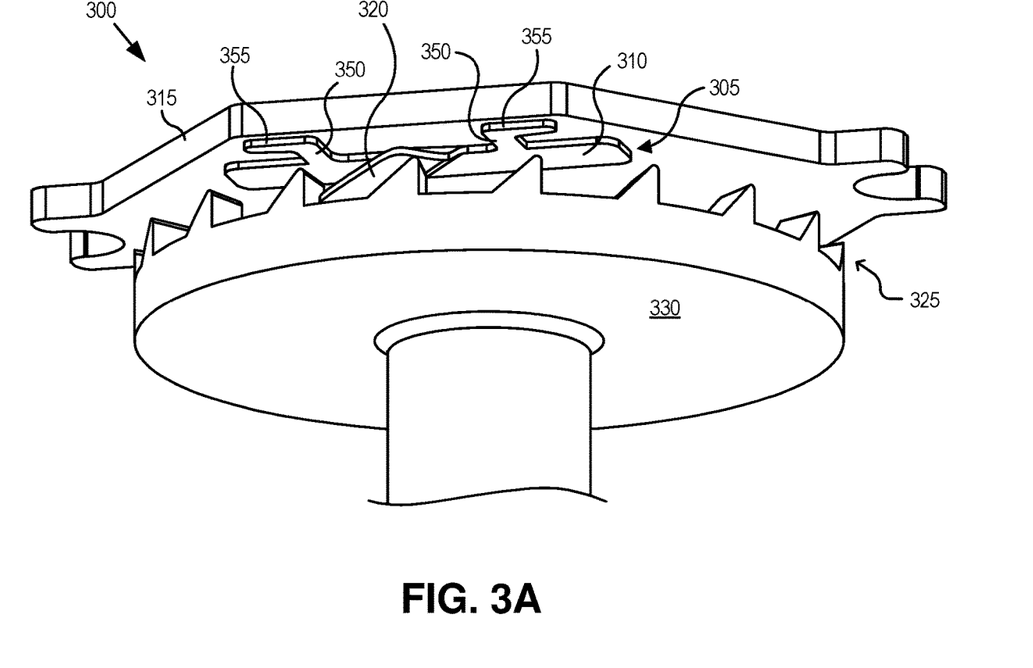
FIG. 3A is a perspective view illustration of a dosage measurement system including a sensing capacitor having an adjustable plate that moves in response to engagement between a lifting tab and an undulation pattern, in accordance with several embodiments of the disclosure.
Figure 3B:
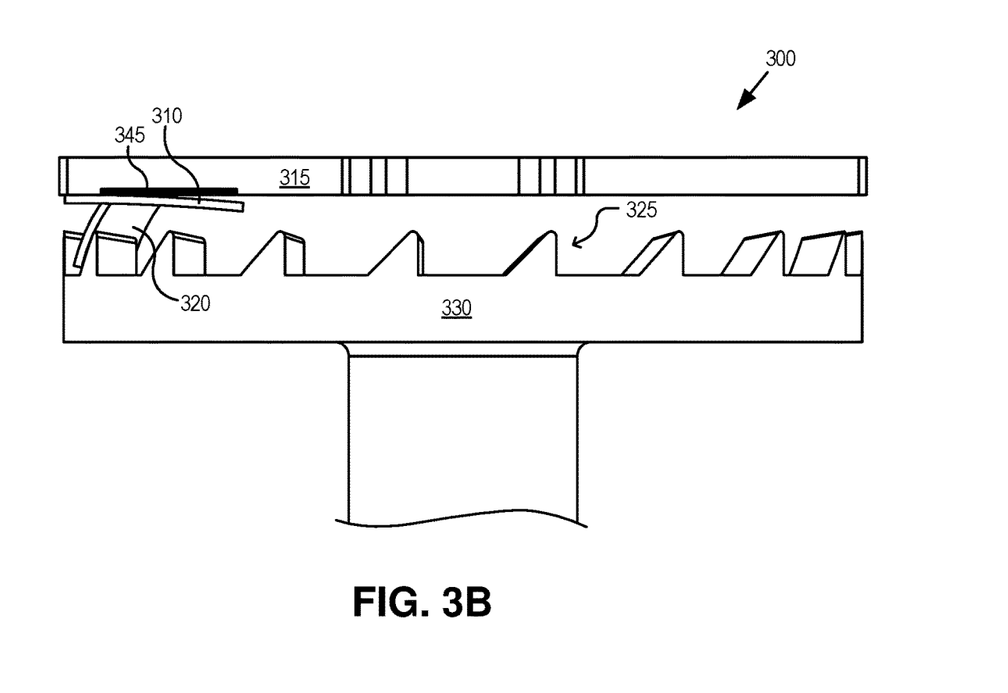
FIG. 3B is a side view illustration of the dosage measurement system showing how the adjustable plate of the sensing capacitor pivots, in accordance with several embodiments of the disclosure.
Figure 3C:
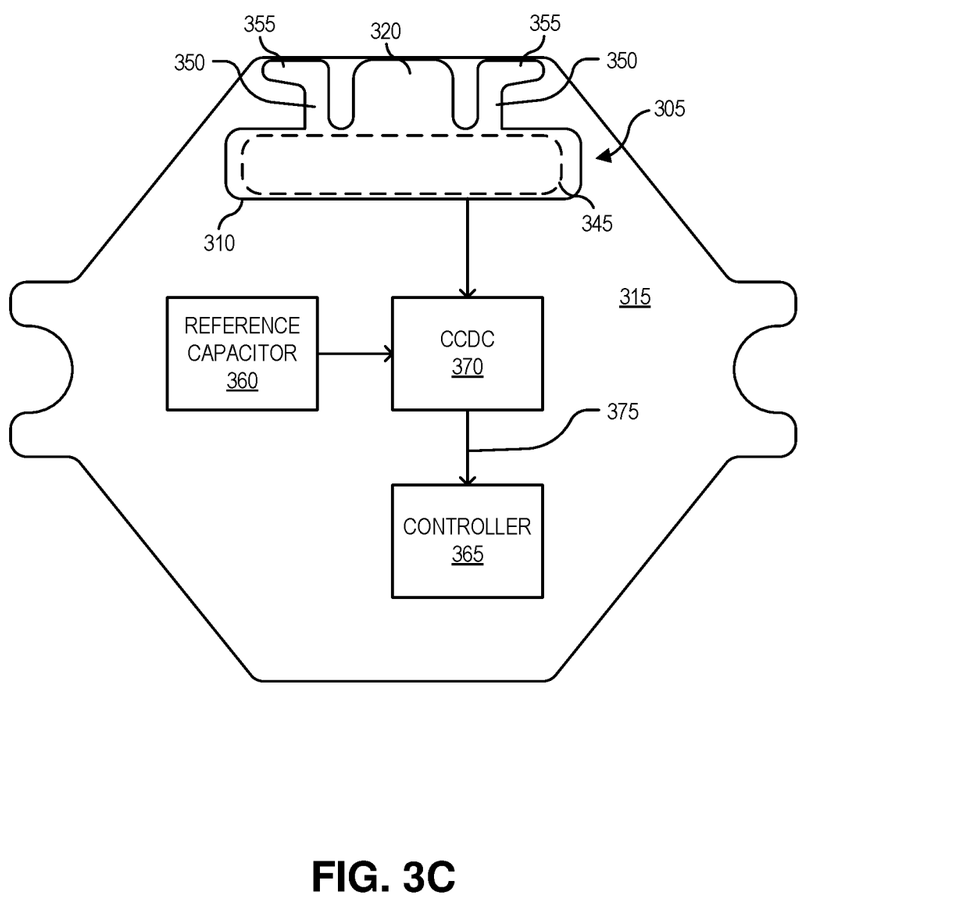
FIG. 3C is a plan view illustration of the substrate including the sensing capacitor and a reference capacitor, in accordance with several embodiments of the disclosure.

FIGS. 3A-C illustrate an example dosage measurement system 300 including a sensing capacitor 305 having an adjustable plate 310 mounted on a substrate 315 that moves in response to engagement between a lifting tab 320 and an undulation pattern 325 on a component 330 (e.g., toothed component), in accordance with several embodiments of the disclosure. FIG. 3A is a perspective view illustration of system 300, while FIG. 3B is a side view and FIG. 3C is a plan view of substrate 315. System 300 is one possible implementation of various components of dosage measurement system 251 illustrated in FIGS. 2A and 2B.

The illustrated embodiment of sensing capacitor 305 includes a dielectric layer disposed between a base plate 345 and adjustable plate 310. In the illustrated embodiment, base plate 345 is stationary and disposed on substrate 315 behind (e.g., hidden under adjustable plate 310). Base plate 345 and adjustable plate 310 form the electrode plates of the capacitor and may be fabricated of a variety of conductive materials (e.g., metal or metal alloy). The dielectric layer may be fabricated of a variety of different insulating materials. In one embodiment, the dielectric layer is a solder mask or solder resist layer disposed over a printed circuit board (PCB) used to implement substrate 315. Base plate 345 may be fabricated as a metal pad on the PCB. Adjustable plate 310 is held in place over base plate 345 via flexible anchor arms 350 which are anchored to mounting pads 355. In one embodiment, mounting pads 355 are solder pads on substrate 315 and flexible anchor arms 350 are soldered to the solder pads. In the illustrated embodiment, flexible anchor arms 350 are integral to adjustable plate 310 and extend between adjustable plate 310 and mounting pads 355. The narrowing length of flexible anchor arms 350 provides a flexible spring that bends adjustable plate 310 away from base plate 345 with a spring force.

Lifting tab 320 attaches to adjustable plate 310, extends therefrom, and provides a contact location for engaging undulation pattern 325. In one embodiment, lifting tab 320 is also an integral component with adjustable plate 310. As lifting table 320 moves over undulation pattern 325, it is pressed up, thereby applying a torsional force on adjustable plate 310 that bends/pivots adjustable plate 310 away from base plate 345 in the illustrated embodiment. The bending/pivoting occurs primarily along the length of flexible anchor arms 350. The changing separation gap between adjustable plate 310 and base plate 345 of sensing capacitor 305 results in a changing capacitance that changes based upon rotational position of substrate 315 relative to component 330.

Undulation pattern 325 is disposed around component 330. Undulation pattern 320 engages lifting tab 320 and physically moves adjustable plate 310 via lifting tab 320 in a reciprocal manner as substrates 330 and 310 rotate relative to each other. Undulation pattern 320 is illustrated as having a sawtooth shape with peaks and valleys that engage lifting tab 320. However, undulation pattern 320 may assume a variety of other shapes including regular or irregular patterns, a sinusoidal shape, or otherwise. Undulation pattern 320 may be an integral portion of component 330 or a distinct component that is attached or otherwise bonded to component 330. Furthermore, FIG. 3A illustrates undulation pattern 325 as rising from component 330; however, undulation pattern 320 may also recess into component 330 or even be cut around a perimeter (e.g., outside edge) of component 330. Undulation pattern 325 may be fabricated of the same material as component 330 or a different material. For example, undulation pattern 325 and/or component 330 may be fabricated of plastic, resin, metal, or otherwise.

FIG. 3C is a plan view illustration of the side of substrate 315 that faces undulation pattern 325 and component 330. In the illustrated embodiment, this side of substrate 315 includes a reference capacitor 360 along with controller 365 and capacitance change detection circuitry (CCDC) 370. It should be appreciated that one or more of reference capacitor 360, controller 365, or CCDC 370 may also be disposed on the backside of substrate 315 opposite the side upon which sensing capacitor 305 is disposed.

CCDC 370 is coupled to sensing capacitor 305 to monitor and measure changes in the capacitance between adjustable plate 310 and base plate 345. CCDC 370 outputs a signal 375 indicative of changes in the capacitance of sensing capacitor 305. Controller 365 is coupled to CCDC 370 to receive signal 375 and track changes in signal 375 for determining a quantity of fluid dispensed by the drug injection pen. Accordingly, controller 365 includes logic that maintains state information for tracking the absolute rotational position or number of revolutions of substrate 315 relative to component 330, which in turn is related to the rotational motion of the dosage injection mechanism in the drug injection pen.

Figure 4A:
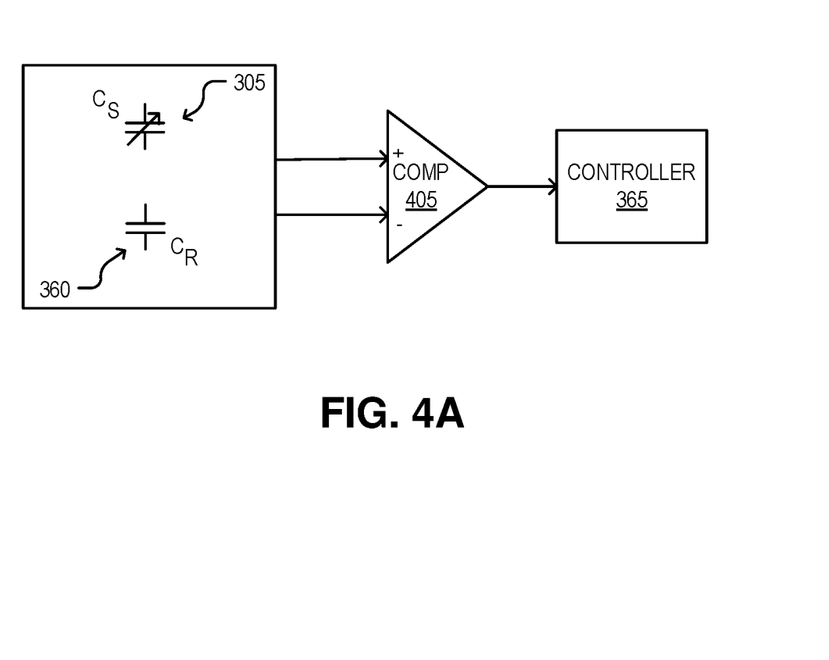
FIG. 4A is a functional block diagram illustrating components of capacitance change detection circuitry, in accordance with an embodiment of the disclosure.

CCDC 370 may be implemented using a variety of different capacitance change detection circuits. FIG. 4A illustrates one example conceptual implementation where CCDC 370 includes a differential comparator 405 coupled to the optional reference capacitor 360 having a fixed capacitance $C_R$ and sensing capacitor 305 having a variable capacitance $C_S$. The differential comparator may be configured to sense a differential capacitance ($C_S$–$C_R$) between reference capacitor 360 and sensing capacitor 305, which has a variable capacitance due to motion of lifting tab 320 by undulation pattern 325. Though not illustrated in FIG. 4A, sensing capacitor 305 and reference capacitor 360 may additionally be coupled to drive circuitry to drive a signal onto the capacitors to generate measurable voltages across sensing capacitor 305 and reference capacitor 360 (e.g., signal generator 415). By overlaying base plate 345 and the base plate of reference capacitor 360 with the same dielectric layer during manufacturing, the differential comparator configuration may be useful to cancel out manufacturing variations in this dielectric layer (e.g., thickness variations) that can occur from one device to the next.

Figure 4B:
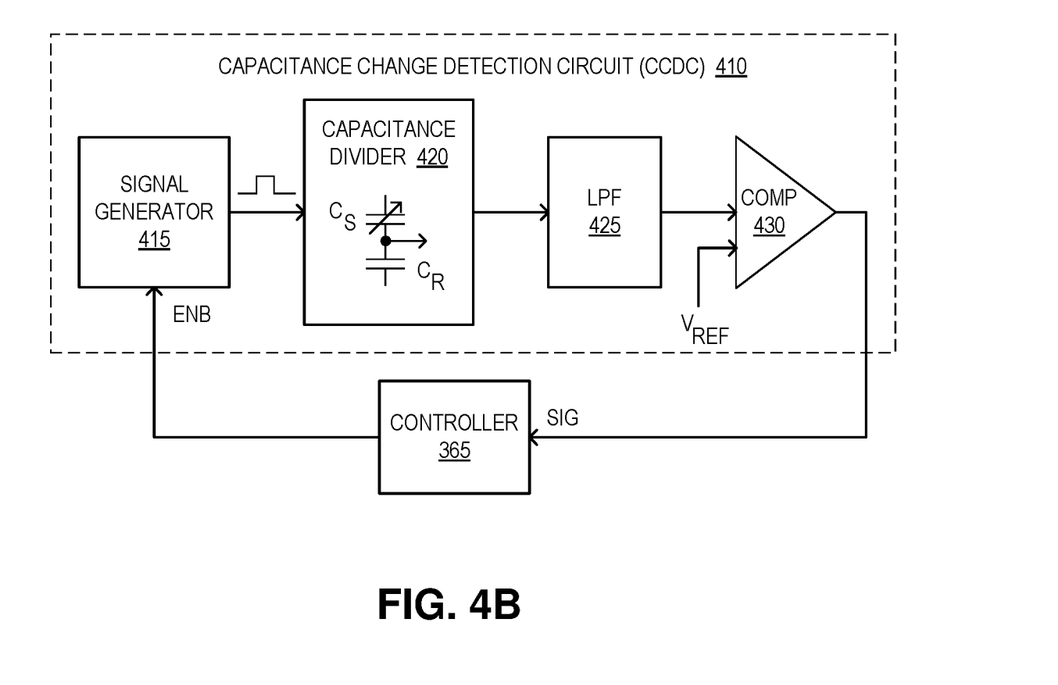
FIG. 4B is a functional block diagram illustrating components of other capacitance change detection circuitry, in accordance with an embodiment of the disclosure.

FIG. 4B illustrates yet another possible implementation of CCDC 370, labelled as CCDC 410. The illustrated embodiment of CCDC 410 includes a signal generator 415, a capacitance divider 420, a low pass filter (LPF) 425, and a comparator 430. Capacitance divider 420 includes sensing capacitor $C_S$ coupled into a divider configuration with reference capacitor $C_R$. During operation, capacitance divider 420 is stimulated by a drive signal (e.g., square wave) generated by signal generator 415. As the capacitance value $C_S$ varies in response to lifting tab 320 and undulation pattern 325, the output of capacitance divider 420 will vary. The output from the capacitance divider 420 is filtered by LPF 425 before being coupled into comparator 430. Comparator 430 compares the low pass filtered signal output from capacitance divider 420 to a reference voltage $V_{REF}$. The output signal (SIG) from comparator 430 is then coupled into controller 365 where its changing value is tracked by controller 365.

FIGS. 4A and 4B merely illustrate two example implementations of CCDC 370. It should be appreciated that any CCDC 370 may be implemented by any variety of circuits capable of measuring and monitoring changes in capacitance. For example, CCDC 370 may be implemented with a capacitance divider circuit, such as the example illustrated in FIG. 4B, by a differential comparator, such as the example illustrated in FIG. 4A, by a relaxation based oscillator, by a signal amplitude modulator, by a signal rise-time modulator, or otherwise. All of these CCDC implementations couple to (or otherwise include) sensing capacitor 305 as a variable capacitance element.

Figure 5:
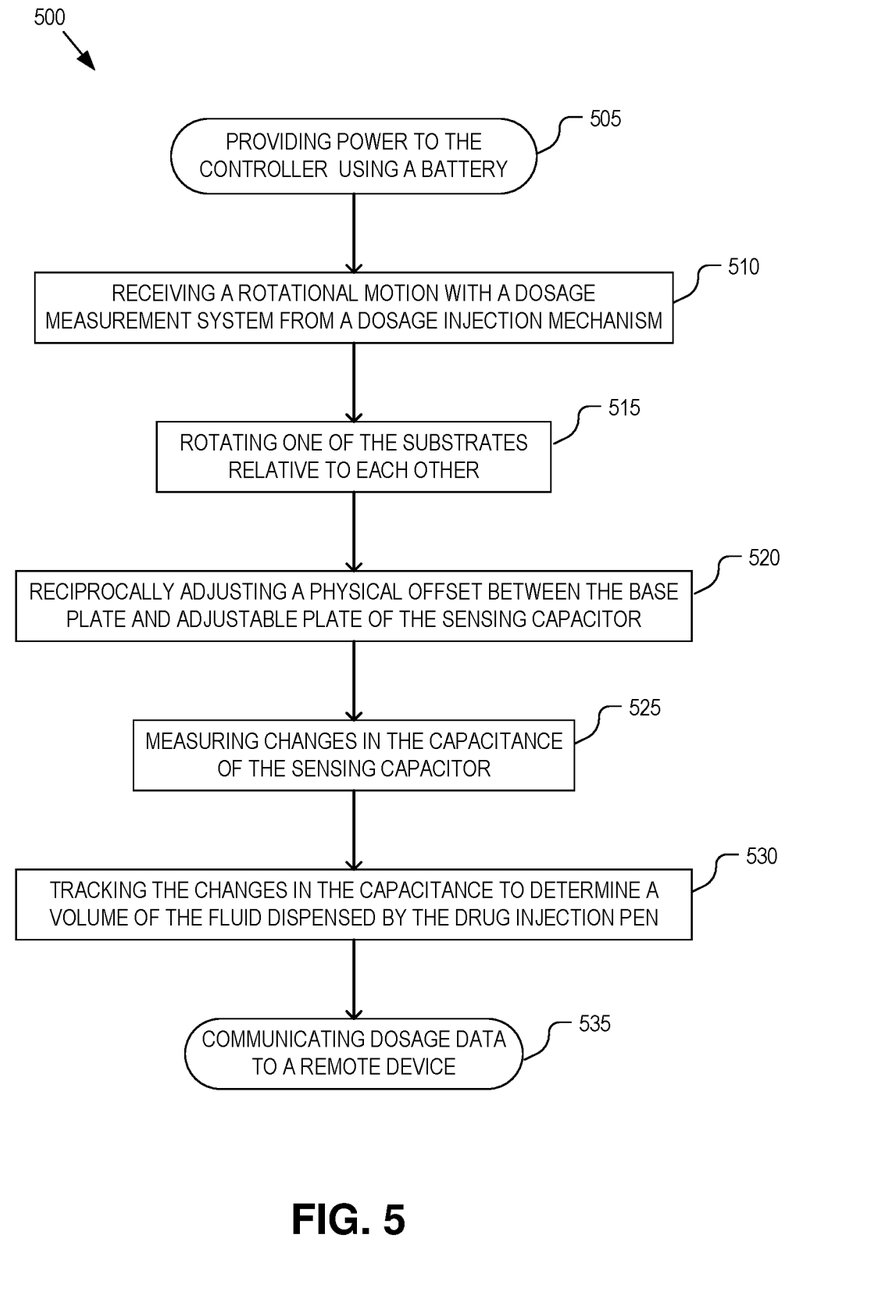
FIG. 5 is a flow chart illustrating a method of operation of the dosage measurement system, in accordance with several embodiments of the disclosure.

FIG. 5 is a flow chart illustrating a method 500 of operation of the dosage measurement system 251 (or 300), in accordance with several embodiments of the disclosure. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel. Further, blocks may be added to or removed from method 500 in accordance with the teaching of the present disclosure.

In a process block 505, power is provided to controller 365 and CCDC 370 using a battery (e.g., a button battery disposed within the battery cage on the backside of substrate 255). Power may be provided when the user presses down on spinner 286 of button 250 attached to the end (opposite the dispensing end) of the drug injection pen. Pressing on the button may turn on or "wake up" electronics 273.

In a process block 510, the rotational motion of the dosage injection mechanism is received by the dosage measurement system 251. The rotational motion is received when the drug injection pen dispenses a fluid. The rotational motion of the dosage injection mechanism is received by dosage measurement system 251 as a rotation of substrate 255 relative to toothed component 253 (process block 515). The rotation of substrate 255 relative to toothed component 253 results in a reciprocal adjustment of a physical offset between base plate 345 and adjustable plate 310 of sensing capacitor 305 (see FIG. 3C) due to engagement of lifting tab 320 with undulation pattern 325 (see FIGS. 3A and 3B). FIG. 3B illustrates how lifting tab 320 causes adjustable plate 310 to pivot back from base plate 345. This pivot action repeats for each peak of undulation pattern 325 and is thus related to the rotational position of the dosage injection mechanism. Although FIGS. 3A and 3B illustrate a pivoting separation that bends along flexible anchor arms 350, other mounting configurations may results in other forms of reciprocal separation between base plate 345 and adjustable plate 310.

In a process block 525, CCDC 370 measures the changes in capacitance $C_S$ of sensing capacitor 305 and controller 365 tracks these changes over a prior of time maintaining state so that an absolute rotational position relative to an initial/zero position can be tracked (process block 530). The absolute rotational position can then be used to determine a volume of the fluid dispensed by the drug injection pen. Finally, in a process block 535, dosage data related to the volume of the fluid dispensed may be communication to a remote device (e.g., processing device 121).

Figure 6:
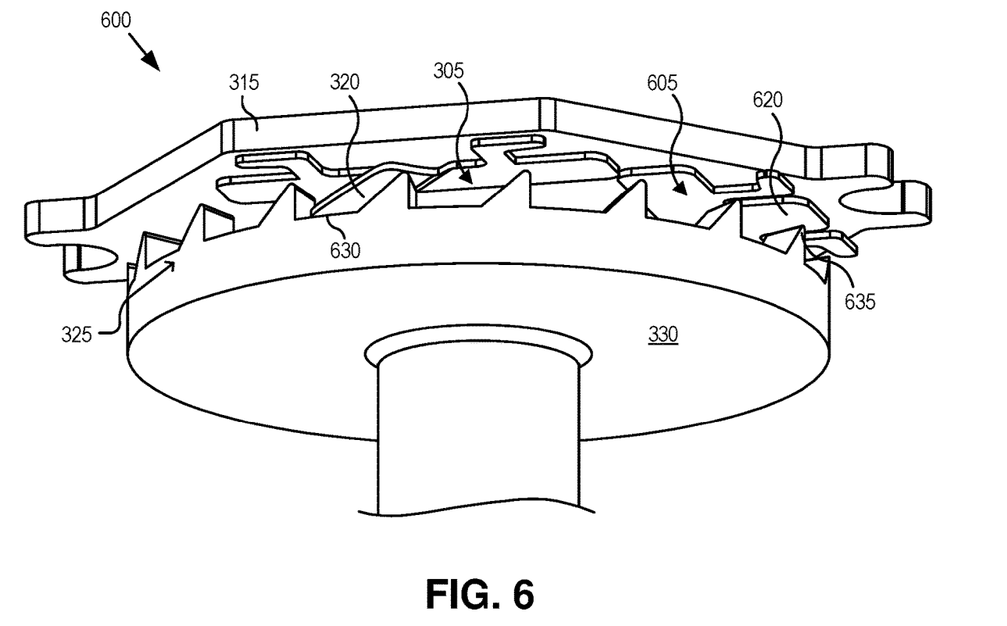
FIG. 6 is a perspective view illustration of a dosage measurement system including two sensing capacitor positioned out of phase for differential sensing of a rotational motion, in accordance with several embodiments of the disclosure.

FIG. 6 is a perspective view illustration of a dosage measurement system 600 including two sensing capacitor 305 and 605 positioned out of phase for differential sensing of a rotational motion, in accordance with several embodiments of the disclosure. Sensing capacitor 305 and 605 are oriented on substrate 315 relative to each other such that their respective lifting tabs 320 and 620 engage undulation pattern 325 out of phase. In other words, lifting tabs 320 and 620 are physically offset from each other such that when lifting tab 320 falls within a valley 630 of undulation pattern 325 lifting tab 620 is pushing again a peak 635 of undulation pattern 325. This out-of-phase offset can provide enhanced differential sensing between sensing capacitors 305 and 605 for greater signal differentiation.

Figure 7:
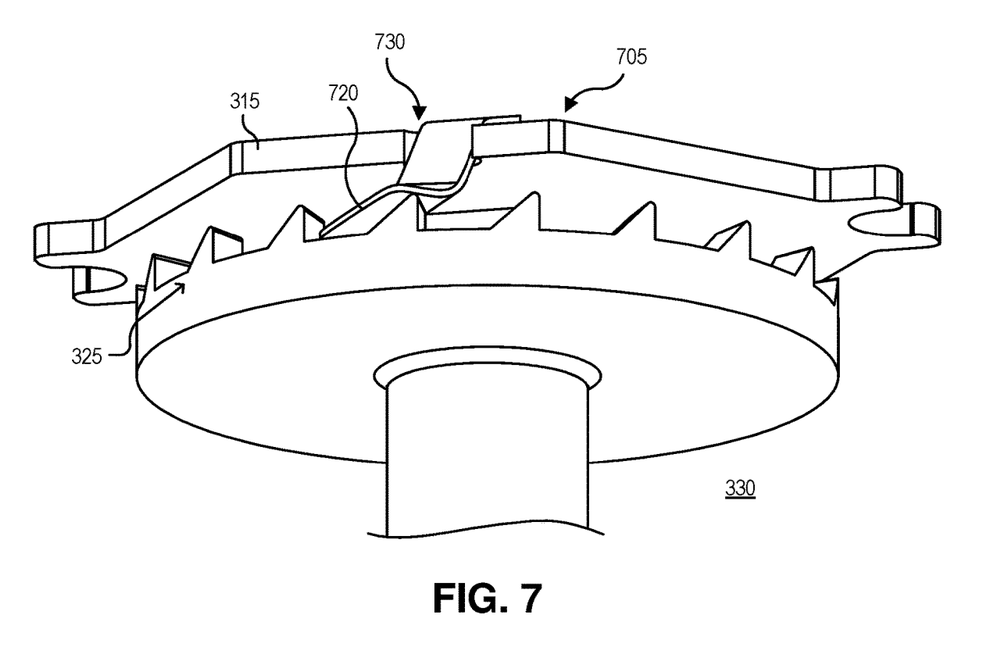
FIG. 7 illustrates a dosage measurement system having the sensing capacitor disposed on a side of a first substrate facing away from the undulation pattern on a second substrate, in accordance with several embodiments of the disclosure.

FIG. 7 illustrates a dosage measurement system 700 having the sensing capacitor 705 (out of sight in the illustrated view) disposed on a side of substrate 315 that is facing away from undulation pattern 325 and component 330, in accordance with several embodiments of the disclosure. In the illustrated embodiment, a lifting tab 720 couples to the adjustable plate of sensing capacitor 705 and extends down around an edge of substrate 315 (e.g., through a notch 730 in the edge of substrate 315) to engage undulation pattern 325. In other embodiments, substrate 315 may include a hole through which lifting tab 720 extends to engage undulation pattern 325. In this configuration, lifting tab 720 reciprocally pushes the adjustable plate away from its base plate by bending the adjustable plate up.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for use with a drug injection pen that dispenses a fluid, the apparatus comprising:
    a dosage measurement system adapted to receive a motion from a dosage injection mechanism disposed within the drug injection pen, the dosage measurement system including:
        a substrate;
        a sensing capacitor disposed on the substrate, the sensing capacitor including a dielectric layer disposed between a base plate and an adjustable plate; and
        a lifting tab attached to the adjustable plate and positioned to engage an undulation pattern disposed on a component attached to the dosage injection mechanism, wherein the lifting tab is adapted to physically change a separation distance between the adjustable plate and the base plate in a reciprocal manner in response to the motion of the dosage injection mechanism and engagement with the undulation pattern, wherein a capacitance of the sensing capacitor changes in response to the engagement of the lifting tab with the undulation pattern and the motion of the dosage injection mechanism.

2. The apparatus of claim 1, further comprising:
    capacitance change detection circuitry coupled to the sensing capacitor, wherein the capacitance change detection circuitry outputs a signal indicative of changes in the capacitance of the sensing capacitor; and
    a controller coupled to the capacitance change detection circuitry, the controller including logic that when executed by the controller causes the controller to perform operations comprising:
        tracking changes in the signal for determining a quantity of the fluid dispensed from the drug injection pen.

3. The apparatus of claim 2, wherein the capacitance change detection circuitry comprises one of:
    a capacitance divider that includes the sensing capacitor and a reference capacitor;
    a relaxation based oscillator that includes the sensing capacitor;
    a signal amplitude modulator that includes the sensing capacitor; or
    a signal rise-time monitor that includes the sensing capacitor.

4. The apparatus of claim 2, wherein the substrate comprises a circuit board and wherein the capacitance change detection circuitry and the controller are also disposed on the circuit board with the sensing capacitor.

5. The apparatus of claim 4, further comprising:
    a reference capacitor disposed on the circuit board and sharing the dielectric layer with the sensing capacitor, wherein the capacitance change detection circuitry comprises a differential comparator coupled to the reference capacitor and the sensing capacitor to cancel out manufacturing variations in the dielectric layer.

6. The apparatus of claim 1, further comprising:
    mounting pads disposed on the substrate; and
    flexible anchor arms extending from the mounting pads to the adjustable plate and holding the adjustable plate over the base plate, wherein the flexible anchor arms flex in response to a force applied to the lifting tab by the undulation pattern thereby moving the adjustable plate.

7. The apparatus of claim 6, wherein the substrate comprises a circuit board and wherein the mounting pads comprise solder pads to which the flexible anchor arms are soldered.

8. The apparatus of claim 1, further comprising:
    a second sensing capacitor disposed on the substrate, the second sensing capacitor including a second adjustable plate; and
    a second lifting tab attached to the second adjustable plate and positioned to also engage the undulation pattern, wherein the second lifting tab is adapted to physically move the second adjustable plate in the reciprocal manner but out of phase from the lifting tab such that the lifting tab aligns with a valley of the undulation pattern when the second lifting tab aligns with a peak of the undulation pattern.

9. The apparatus of claim 1, wherein the sensing capacitor is disposed on either:
    a first side of the substrate that faces towards the undulation pattern; or
    a second side of the substrate that faces away from the undulation pattern and the lifting tabs extends through a hole in the substrate or around an edge of the substrate to engage the undulation pattern.

10. The apparatus of claim 1, further comprising:
    a housing shaped to attach to the drug injection pen, wherein the first substrate, the sensing capacitor, and the lifting tab are at least partially disposed within the housing.

11. The apparatus of claim 10, wherein the housing is shaped to attach to an end of the drug injection pen that is pressed by a thumb while dispensing the fluid.

12. The apparatus of claim 1, wherein the undulation pattern comprises one of a sawtooth shape or a sinusoidal shape, and wherein the undulation pattern rises from the component, recesses into the component, or is cut around a perimeter of the component.

13. A method of measuring a volume of a fluid dispensed from a drug injection pen, comprising:
    receiving a motion at a dosage measurement system disposed at least in part in a button attached to an end of the drug injection pen, the motion received from a dosage injection mechanism disposed within the drug injection pen when the drug injection pen dispenses a fluid;

reciprocally adjusting a physical offset between an adjustable plate of a sensing capacitor and a base plate of the sensing capacitor with a lifting tab attached to the adjustable plate, wherein the lifting tab engages an undulation pattern on a component attached to the dosage injection mechanism; and measuring changes in a capacitance of the sensing capacitor, wherein the capacitance changes in response to engagement of the lifting tab with the undulation pattern while the dosage injection mechanism dispenses the fluid.

14. The method of claim 13, further comprising:
tracking the changes in the capacitance over a time period, wherein the changes tracked enable determination of the volume of the fluid dispensed from the drug injection pen over the time period.

15. The method of claim 14, wherein the sensing capacitor, capacitance change detection circuitry for measuring the changes in the capacitance of the sensing capacitor, and a controller for tracking the changes in the capacitance over the time period are all disposed on a common substrate.

16. The method of claim 13, wherein measuring the changes in the capacitance comprises:
differentially comparing the capacitance of the sensing capacitor to a reference capacitance of a reference capacitor that shares a common dielectric layer with the sensing capacitor to cancel out manufacturing variations in the common dielectric layer.

17. The method of claim 13, wherein measuring the changes in the capacitance comprises:
differentially comparing the capacitance of the sensing capacitor to a second capacitance of a second sensing capacitor disposed on a common substrate with the sensing capacitor, wherein a second lifting tab attached to a second adjustable plate of the second sensing capacitor engages the undulation pattern out of phase from the lifting tab such that the lifting tab aligns with a valley of the undulation pattern when the second lifting tab aligns with a peak of the undulation pattern.

18. The method of claim 13, wherein the undulation pattern comprises one of a sawtooth shape or a sinusoidal shape, and wherein the undulation pattern rises from the component, recesses into the component, or is cut around a perimeter of the component.

19. The method of claim 13, wherein the sensing capacitor is disposed on a substrate and wherein reciprocally adjusting the physical offset between the adjustable plate relative to the base plate with the lifting tab comprises:
flexing flexible anchor arms that extend from mounting pads disposed on the substrate to the adjustable plate, wherein the flexible anchor arms hold the adjustable plate over the base plate with a spring force.

20. The method of claim 19, wherein reciprocally adjusting the physical offset between the adjustable plate relative to the base plate with the lifting tab comprises:
pivoting the adjustable plate when the undulation pattern presses against the lifting tab.

* * * * *